United States Patent
Suuronen et al.

(10) Patent No.: US 11,058,379 B2
(45) Date of Patent: Jul. 13, 2021

(54) X-RAY IMAGING UNIT FOR MEDICAL IMAGING

(71) Applicant: PaloDEx Group Oy, Tuusula (FI)

(72) Inventors: Esa Suuronen, Kerava (FI); Sami Vartiainen, Vantaa (FI)

(73) Assignee: PaloDEx Group Oy, Tuusula (FI)

( * ) Notice: Subject to any disclaimer, the term of this patent is extended or adjusted under 35 U.S.C. 154(b) by 94 days.

(21) Appl. No.: 15/873,516

(22) Filed: Jan. 17, 2018

(65) Prior Publication Data

US 2018/0140267 A1 May 24, 2018

Related U.S. Application Data

(63) Continuation of application No. 14/640,626, filed on Mar. 6, 2015, now Pat. No. 9,888,891.

(30) Foreign Application Priority Data

Jun. 26, 2014 (FI) ...................................... 20145617
Jan. 2, 2015 (FI) ...................................... 20155002

(Continued)

(51) Int. Cl.
*A61B 6/00* (2006.01)
*A61B 6/03* (2006.01)
(Continued)

(52) U.S. Cl.
CPC ............ *A61B 6/4452* (2013.01); *A61B 6/032* (2013.01); *A61B 6/0407* (2013.01); *A61B 6/14* (2013.01); *A61B 6/4007* (2013.01); *A61B 6/4266* (2013.01)

(58) Field of Classification Search
CPC ....... A61B 6/14; A61B 6/4007; A61B 6/4452; A61B 6/4429; A61B 6/4435;
(Continued)

(56) References Cited

U.S. PATENT DOCUMENTS 4,365,340 A * 12/1982 Nishikawa ............. A61B 6/501
378/197
4,675,888 A 6/1987 Gastrin
(Continued)

FOREIGN PATENT DOCUMENTS

CN 101547644 A 9/2009
EP 2609861 7/2013
(Continued)

OTHER PUBLICATIONS

Finnish Office Action issued in corresponding Finnish Application No. 20145617 dated Jan. 28, 2015.
(Continued)

*Primary Examiner* — Dani Fox
*Assistant Examiner* — Soorena Kefayati
(74) *Attorney, Agent, or Firm* — Andrus Intellectual Property Law, LLP

(57) ABSTRACT

The application relates to an X-ray imaging unit for a medical imaging. The unit includes a rotating part with a first X-ray source and an X-ray imaging detector unit configured to provide an image with at least a rotational movement (R) around a rotation axis of the rotating part. The unit includes an upper shelf configured to enable the rotating part to move with respect to the upper shelf with a linear movement (L) and to be attached to a column with a pivoting joint for enabling a pivot movement (P) of the upper shelf around the column. The rotating part is configured to be positioned by the linear movement and the pivot movement during the imaging.

14 Claims, 11 Drawing Sheets

(30) Foreign Application Priority Data

| Jan. 2, 2015 | (FI) | .................................... | 20155003 |
| Jan. 2, 2015 | (FI) | .................................... | 20155004 |
| Jan. 2, 2015 | (FI) | .................................... | 20155005 |

(51) Int. Cl.
*A61B 6/04* (2006.01)
*A61B 6/14* (2006.01)

(58) Field of Classification Search
CPC ..... A61B 6/4458; A61B 6/4464; A61B 6/501; A61B 6/032; A61B 6/0407; A61B 6/4266
See application file for complete search history.

(56) References Cited

U.S. PATENT DOCUMENTS

| 4,907,251 | A | * | 3/1990 | Mork .................. A61B 6/08 378/39 |
| 5,058,147 | A | | 10/1991 | Nishikawa et al. |
| 5,506,879 | A | | 4/1996 | Mori et al. |
| 5,511,106 | A | | 4/1996 | Doebert et al. |
| 5,921,927 | A | * | 7/1999 | McArdle .................. A61B 6/14 600/425 |
| 6,169,780 | B1 | * | 1/2001 | Yoshimura .............. A61B 6/14 378/38 |
| 6,466,641 | B1 | * | 10/2002 | Virta .................... A61B 6/14 378/38 |
| 7,197,109 | B2 | | 3/2007 | Rotondo et al. |
| 7,424,091 | B2 | * | 9/2008 | Park .................... A61B 6/14 378/39 |
| 7,486,767 | B2 | | 2/2009 | Sonobe et al. |
| 7,577,232 | B2 | | 8/2009 | Tachibana |
| 7,945,016 | B2 | | 5/2011 | Bothorel et al. |
| 7,961,841 | B2 | | 6/2011 | Ro et al. |
| 8,005,186 | B2 | | 8/2011 | Lee et al. |
| 8,005,187 | B2 | | 8/2011 | Suzuki et al. |
| 8,396,186 | B2 | | 3/2013 | Tomoe |
| 8,503,604 | B2 | | 8/2013 | Inglese |
| 8,979,364 | B2 | | 3/2015 | Bothorel et al. |
| 8,979,366 | B2 | | 3/2015 | Tomoe |
| 9,060,716 | B2 | * | 6/2015 | Bianconi .............. A61B 6/4007 |
| 9,265,469 | B2 | * | 2/2016 | Baldini ................ A61B 6/4266 |
| 2002/0106053 | A1 | * | 8/2002 | Suuronen .............. A61B 6/06 378/39 |
| 2004/0076263 | A1 | | 4/2004 | De Godzinsky et al. |
| 2004/0190678 | A1 | * | 9/2004 | Rotondo ................ A61B 6/14 378/38 |
| 2006/0056594 | A1 | * | 3/2006 | Sonobe ................ A61B 6/105 378/117 |
| 2007/0030951 | A1 | * | 2/2007 | Park .................... A61B 6/5247 378/38 |
| 2008/0310584 | A1 | | 12/2008 | Hey et al. |
| 2009/0168966 | A1 | * | 7/2009 | Suzuki ................ A61B 6/4233 378/116 |
| 2009/0196395 | A1 | * | 8/2009 | Gregorio ................ A61B 6/14 378/38 |
| 2009/0245461 | A1 | * | 10/2009 | Lee ........................ A61B 6/032 378/38 |
| 2010/0074402 | A1 | | 3/2010 | Bothorel et al. |
| 2010/0074403 | A1 | | 3/2010 | Inglese et al. |
| 2010/0278299 | A1 | | 11/2010 | Loustauneau et al. |
| 2011/0142198 | A1 | * | 6/2011 | Cekov ................ A61B 6/4411 378/38 |
| 2011/0142199 | A1 | * | 6/2011 | Kantor ................ A61B 6/4441 378/39 |
| 2011/0222646 | A1 | | 9/2011 | Suzuki et al. |
| 2012/0039436 | A1 | * | 2/2012 | Bothorel ................ A61B 6/14 378/11 |
| 2012/0093284 | A1 | | 4/2012 | Takemoto et al. |
| 2012/0148014 | A1 | | 6/2012 | Vartiainen |
| 2012/0243762 | A1 | | 9/2012 | Kanerva et al. |
| 2012/0321035 | A1 | | 12/2012 | Muller |
| 2013/0089177 | A1 | * | 4/2013 | Baldini ................ A61B 6/14 378/39 |
| 2013/0136226 | A1 | | 5/2013 | Tomoe et al. |
| 2013/0170612 | A1 | * | 7/2013 | Bianconi .............. A61B 6/032 378/9 |
| 2015/0004558 | A1 | | 1/2015 | Inglese et al. |
| 2015/0010126 | A1 | * | 1/2015 | Rotondo ................ A61B 6/06 378/19 |
| 2015/0265237 | A1 | | 9/2015 | Keeve et al. |
| 2015/0289833 | A1 | * | 10/2015 | Yamanaka ........... A61B 6/5241 378/19 |
| 2016/0345916 | A1 | | 12/2016 | Lim et al. |

FOREIGN PATENT DOCUMENTS

| FI | 20145617 | 12/2015 |
| JP | 2001518341 | 10/1997 |
| JP | 2013138865 | 12/2011 |
| JP | 2013244187 | 5/2012 |

OTHER PUBLICATIONS

Finnish Search Report from corresponding Finnish Application No. 20145617 dated Jan. 28, 2015.
Finnish Search Report from corresponding Finnish Application No. 20155005 dated Dec. 12, 2016.
Japanese Office Action issued in corresponding Japanese Patent Application No. 2015-128894, dated Sep. 18, 2018.
Chinese Search Report issued for corresponding Chinese Patent Application No. 201510492752.9, dated Feb. 2, 2019.

* cited by examiner

X-RAY IMAGING UNIT FOR MEDICAL IMAGING

CROSS REFERENCE TO RELATED APPLICATIONS

This application is a continuation of U.S. Pat. No. 14/640,626 filed Mar. 6, 2015, which application was published as U.S. Pat No. 2015/0374320 on Dec. 31, 2015 in the English language, which application claims priority to Finnish Patent Application Nos. 20155002, 20155003, 20155004, and 20155005, filed Jan. 2, 2015, and Finnish Patent Application No. 20145617, filed Jun. 26, 2014, the applications of which are incorporated herein by reference, in their entireties.

TECHNICAL FIELD

The application relates generally to an X-ray imaging unit for medical imaging.

BACKGROUND

FIGS. 1a-1b represent a modern digital Panoramic/Cephalometric/Cone Beam Computed Tomography (CBCT) combination unit 100 having typically a column 140 that includes an up and down movement Z to adapt a height of the unit 100 to a height of a patient for Panoramic, Cephalometric, and CBCT imaging modes.

An upper shelf 150 of the unit 100 is attached to the column 140 e.g. with a fixed joint. The upper shelf 150 supports a rotating part 120.

The rotating part 120—so-called gantry—has typically a form of a letter C incorporating an X-ray source 124 on one end and an X-ray imaging detector unit 126 on the other end. The rotating part 120 rotates R typically up to 400 degrees around a rotation axis 122.

The X-ray source 124 is common for all the three imaging modes and an X-ray beam limiting device 128 is attached in front of the X-ray source 124.

The detector unit 126 can consist of one or two detectors. The one-detector unit 126 can comprise one Cephalometric detector, which enables also the Panoramic imaging, one Panoramic/CBCT/Cephalometric combination detector, or one shot detector configured to be used in Cephalometric imaging. In two-detector cases, the detector unit 126 can comprise one Cephalometric detector, which enables also the Panoramic imaging, and the CBCT detector. There are several ways to attach the detectors in respect to each other and to change the detector that is located within an X-ray beam.

During imaging, the beam limiting device 128 controls a size and shape of the X-ray beam so that it matches any requirements of a selected imaging mode, selected image size, and related detector size.

The rotation axis 122 fixes the rotation part 120 to the upper shelf 150 and it is typically attached to at least one linear movement so that the rotation axis 122 and, thus, a rotation center of the rotation part 120 in respect to the upper shelf 150 can be adjusted along a Y-movement that is parallel to the upper shelf 150 during the imaging. Furthermore, there can be a second linear X-movement perpendicular to the first one so that the rotation axis 122 can be positioned within a plane defined the linear movements X, Y.

In addition, there can be even a third N-movement that moves a fixing point of the rotation axis 122 an respect to the rotation part 120. Moving the rotation axis 122 along the X-ray beam NA may be used to change a magnification within the Panoramic and CBCT imaging modes. Moving the rotation axis 122 perpendicular to the X-ray beam NP enables a change between offset scanning and symmetrical scanning in the CBCT imaging, thus, affecting the Field Of View (FOV).

A Cephalometric arm 160 is used to attach a Cephalometric head 162 to the unit 100. It has typically a dedicated X-ray imaging detector 164 at one end and a secondary collimator 166 at the other end. Between these two main parts 164, 166 hang Cephalometric patient positioning support parts 168, 169, which consist of ear rods 168 and a nose (nasion) support 169. The patient's head is supported from an outer part of an ear canal with the ear rods 168 and from a nose using the corresponding support 169.

The Cephalometric X-ray detector 164 is attached to the head 162 with a $C_d$-movement that moves the detector 164 perpendicularly to the X-ray beam. Alternatively, it is possible to perform the Cephalometric imaging by a one shot technique, when the detector 164 is sufficiently large.

The Cephalometric secondary collimator 166 is also attached to the head 162 with a C-movement that is parallel to the Cd-movement and, thus, also perpendicular to the X-ray beam.

The support parts 168, 169 are attached to the head 162 in a manner that enables them to rotate to two main imaging positions: the lateral and posterior anterior (PA) projections. The lateral projection is basically a side view and the PA projection is from a back-to-front view of a skull.

For Panoramic and CBCT imaging, a patient is typically supported by means of a lower shelf 142 and possibly also by means of a temple support 143. The support points are typically a tip of a chin and a forehead or temple of a patient.

The Panoramic imaging unit 100 uses the rotation R and linear X-, Y-, or both X- and Y-movements during the scan resulting in a Panoramic image. Furthermore, depending on the sensor technology used, the image is clocked out using Time Delay Integration (TDI) or full frame read-out mode of the detector. The Panoramic (sharp) layer is defined by the velocities of the movements and, in the case of the readout rate of the Panoramic detector. When using a full frame detector, the final shape of the layer is calculated on the computer after the scan. Rotation angle is typically about 270 degrees.

In the unit 100 the CBCT imaging is typically implemented by using a rotation movement R and reading out the CBCT detector with a full frame mode. Thus, projection X-ray images of the Region Of Interest (ROI) are typically produced in a way that the center of the ROI and the rotation movement R coincide. The effective rotation angle (aperture) is ranging typically from approximately 180 to 360 degrees depending on the unit 100.

In the Cephalometric imaging the patient is supported by patient positioning structures 168, 169 located at the Cephalometric head 162 of the unit 100. The X-ray beam is arranged to scan the patient's head with a combination of rotation R and linear Y-movement. The beam is then further collimated by the secondary collimator 166 and finally captured by the Cephalometric detector 164, which both move in synchronism with the beam.

SUMMARY

One object of the invention is to eliminate drawbacks of the known Panoramic/Cephalometric/Computed Tomography (CT) combination units and to provide a cheaper and more compact X-ray imaging unit for medical imaging.

One embodiment of the invention is an X-ray imaging unit for medical imaging, which includes a rotating part including a first X-ray source and an X-ray imaging detector unit configured to provide an image by means of at least a rotational movement around a rotation axis of the rotating part, and an upper shelf for supporting the rotating part. The upper shelf is configured to enable the rotating part to move with respect to the upper shelf by means of a linear movement and to be attached to a column with a pivoting joint for enabling a pivot movement (P) of the upper shelf around the column. The rotating part is configured to be positioned by the linear movement and the pivot movement during the imaging.

The term "medical imaging" refers to e.g. a dental, extraoral, oral, maxillofacial, or ears, nose, and throat imaging.

One embodiment of the invention is a method for controlling an X-ray imaging unit, which unit includes a rotating part comprising a first X-ray source and an X-ray imaging detector unit configured to provide an image by means of at least a rotational movement around a rotation axis of the rotating part, and an upper shelf for supporting the rotating part. The upper shelf is configured to enable the rotating part to move with respect to the upper shelf by means of a linear movement and to be attached to a column with a pivoting joint for enabling a pivot movement of the upper shelf around the column. The method includes positioning the rotating part by the linear movement and the pivot movement during the imaging.

One embodiment of the invention is a computer program for controlling an X-ray imaging unit when the computer program is run in a computer. The unit includes a rotating part which includes a first X-ray source and an X-ray imaging detector unit configured to provide an image by means of at least a rotational movement around a rotation axis of the rotating part, and an upper shelf for supporting the rotating part. The upper shelf is configured to enable the rotating part to move with respect to the upper shelf by means of a linear movement and to be attached to a column with a pivoting joint for enabling a pivot movement of the upper shelf around the column. The computer program includes positioning code for positioning the rotating part by the linear movement and the pivot movement during the imaging.

One embodiment of the invention is a tangible non-volatile computer readable medium which includes a computer program for controlling an X-ray imaging unit when the computer program is run in a computer. The unit includes a rotating part comprising a first X-ray source and an X-ray imaging detector unit configured to provide an image by means of at least a rotational movement around a rotation axis of the rotating part, and an upper shelf for supporting the rotating part. The upper shelf is configured to enable the rotating part to move with respect to the upper shelf by means of a linear movement and to be attached to a column with a pivoting joint for enabling a pivot movement of the upper shelf around the column. The computer program includes positioning code for positioning the rotating part by the linear movement and the pivot movement during the imaging.

One embodiment of the invention is an X-ray imaging unit for a medical imaging which unit comprises a rotating part comprising a first X-ray source and an X-ray imaging detector unit configured to provide an image by means of at least a rotational movement around a rotation axis of the rotating part. The rotating part comprising a Cephalometric collimator for the Cephalometric imaging, and the Cephalometric collimator and a Cephalometric detector, which is configured to provide a Cephalometric image and which is attached to the detector unit of the rotating part, are used for providing a Cephalometric image.

One embodiment of the invention is a method for controlling an X-ray imaging unit, which comprises a rotating part comprising a first X-ray source and an X-ray imaging detector unit configured to provide an image by means of at least a rotational movement around a rotation axis of the rotating part. The method comprises using a Cephalometric collimator and a Cephalometric detector, which is configured to provide a Cephalometric image and which is attached to the detector unit of the rotating part, for providing a Cephalometric image, the Cephalometric collimator being associated with the rotating part.

One embodiment of the invention is a computer program for controlling an X-ray imaging unit, when the computer program is run in a computer. The unit comprises a rotating part comprising a first X-ray source and an X-ray imaging detector unit configured to provide an image by means of at least a rotational movement around a rotation axis of the rotating part. The computer program comprises a use code for using a Cephalometric collimator and a Cephalometric detector, which is configured to provide a Cephalometric image and which is attached to the detector unit of the rotating part, for providing a Cephalometric image, the Cephalometric collimator being associated with the rotating part.

One embodiment of the invention is a tangible non-volatile computer readable medium comprising a computer program for controlling an X-ray imaging unit, when the computer program is run in a computer. The unit comprises a rotating part comprising a first X-ray source and an X-ray imaging detector unit configured to provide an image by means of at least a rotational movement around a rotation axis of the rotating part. The computer program comprises a use code for using a Cephalometric collimator and a Cephalometric detector, which is configured to provide a Cephalometric image and which is attached to the detector unit of the rotating part, for providing a Cephalometric image, the Cephalometric collimator being associated with the rotating part.

One embodiment of the invention is an X-ray imaging unit for a medical imaging, which unit comprises a rotating part comprising a first X-ray source and an X-ray imaging detector unit configured to provide an image by means of at least a rotational movement around a rotation axis of the rotating part, and an upper shelf for supporting the rotating part. The upper shelf is configured to enable the rotating part to move with respect to the upper shelf by means of a linear movement and to be attached to a column with a pivoting joint for enabling a pivot movement of the upper shelf around the column. The rotating part comprising a Cephalometric collimator for the Cephalometric imaging, and the detector unit and the Cephalometric collimator are positioned by means of at least one of the rotational, linear, and pivot movements of the rotating part during the Cephalometric imaging.

One embodiment of the invention is a method for controlling an X-ray imaging unit, which comprises a rotating part comprising a first X-ray source and an X-ray imaging detector unit configured to provide an image by means of at least a rotational movement around a rotation axis of the rotating part, and an upper shelf for supporting the rotating part. The upper shelf is configured to enable the rotating part to move with respect to the upper shelf by means of a linear movement and to be attached to a column with a pivoting joint for enabling a pivot movement of the upper shelf around the column. The rotating part comprising a Cephalometric collimator for a Cephalometric imaging. The method comprises positioning the detector unit and the Cephalometric collimator by means of at least one of the rotational, linear, and pivot movements of the rotating part during the Cephalometric imaging.

One embodiment of the invention is a computer program tier controlling an X-ray imaging unit, when the computer program is run in a computer. The unit comprises a rotating part comprising a first X-ray source and an X-ray imaging detector unit configured to provide an image by means of at least a rotational movement around a rotation axis of the rotating part, and an upper shelf for supporting the rotating part. The upper shelf is configured to enable the rotating part to move with respect to the upper shelf by means of a linear movement and to be attached to a column with a pivoting joint for enabling a pivot movement of the upper shelf around the column. The rotating part comprising a Cephalometric collimator for a Cephalometric imaging. The computer program comprises a positioning code for positioning the detector unit and the Cephalometric collimator by means of at least one of the rotational, linear, and pivot movements of the rotating part during the Cephalometric imaging.

One embodiment of the invention is a tangible non-volatile computer readable medium comprising a computer program for controlling an X-ray imaging unit, when the computer program is run in a computer. The unit comprises a rotating part comprising a first X-ray source and an X-ray imaging detector unit configured to provide an image by means of at least a rotational movement around a rotation axis of the rotating part, and an upper shelf for supporting the rotating part. The upper shelf is configured to enable the rotating part to move with respect to the upper shelf by means of a linear movement and to be attached to a column with a pivoting joint for enabling a pivot movement of the upper shelf around the column. The rotating part comprising a Cephalometric collimator for a Cephalometric imaging. The computer program comprises a positioning code for positioning the detector unit and the Cephalometric collimator by means of at least one of the rotational, linear, and pivot movements of the rotating part during the Cephalometric imaging.

One embodiment of the invention is an X-ray imaging unit for a medical imaging, which unit comprises a rotating part comprising a first X-ray source and an X-ray imaging detector unit configured to provide an image by means of at least a rotational movement around a rotation axis of the rotating part, and an upper shelf for supporting the rotating part. The upper shelf is attached to a column. The unit further comprises a Cephalometric head comprising a Cephalometric patient support, which is configured to support a patient to be imaged, and a first arm tear attaching the Cephalometric head to a first distance from the column for the Cephalometric imaging, which is provided by means of a detector configured to provide a Cephalometric image and to be attached to the rotating part.

One embodiment of the invention is a method for controlling an X-ray imaging unit, which comprises a rotating part comprising a first X-ray source and an X-ray imaging detector unit configured to provide an image by means of at least a rotational movement around a rotation axis of the rotating part, and an upper shelf for supporting the rotating part. The upper shelf is attached to a column. The method comprises supporting a patient to be imaged by means of a Cephalometric head, which comprises a Cephalometric patient support, and attaching the Cephalometric head to a first distance from the column by means of a first arm for the Cephalometric imaging, which is provided by means of a detector configured to provide a Cephalometric image and to be attached to the rotating pan.

One embodiment of the invention is a computer program for controlling an X-ray imaging unit, when the computer program is run in a computer. The unit comprises a rotating part comprising a first X-ray source and an X-ray imaging detector unit configured to provide an image by means of at least a rotational movement around a rotation axis of the rotating part, and an upper shelf for supporting the rotating part. The upper shelf is attached to a column. The computer program comprises a supporting code for supporting a patient to be imaged by means of a Cephalometric head, which comprises a Cephalometric patient support, and an attaching code for attaching the Cephalometric head to a first distance from the column by means of a first arm for the Cephalometric imaging, which is provided by means of a detector configured to provide a Cephalometric image and to be attached to the rotating part.

One embodiment of the invention is a tangible non-volatile computer readable medium comprising a computer program a computer program for controlling an X-ray imaging unit, when the computer program is run in a computer. The unit comprises a rotating part comprising a first X-ray source and an X-ray imaging detector unit configured to provide an image by means of at least a rotational movement around a rotation axis of the rotating part, and an upper shelf for supporting the rotating part. The upper shelf is attached to a column. The computer program comprises a supporting code for supporting a patient to be imaged by means of a Cephalometric head, which comprises a Cephalometric patient support, and an attaching code for attaching the Cephalometric head to a first distance from the column by means of a first arm for the Cephalometric imaging, which is provided by means of a detector configured to provide a Cephalometric image and to be attached to the rotating part.

One embodiment of the invention is an X-ray imaging unit for a medical imaging, which unit comprises a rotating part comprising a first X-ray source and an X-ray imaging detector unit configured to provide an image by means of at least a rotational movement around a rotation axis of the rotating part. The detector unit comprising at least one detector configured to provide a Panoramic image, a computed tomography image, and a Cephalometric image, and the rotating part further comprising moving means configured to move the at least one detector relative to the rotating part for positioning the at least one detector for the imaging.

One embodiment of the invention is a method for controlling an X-ray imaging unit, which unit comprises a rotating part comprising a first X-ray source and an X-ray imaging detector unit configured to provide an image by means of at least a rotational movement around a rotation axis of the rotating part. The detector unit comprising at least one detector configured to provide a Panoramic image, a computed tomography image, and a Cephalometric image, and the rotating part further comprising moving means. The method comprises positioning by means of the moving means the at least one detector relative to the rotating part for the imaging and providing the Panoramic, computed tomography, or Cephalometric image by means of the at least one detector.

One embodiment of the invention is a computer program for controlling an X-ray imaging unit, when the computer program is run in a computer. The unit comprises a rotating part comprising a first X-ray source and an X-ray imaging detector unit configured to provide an image by means of at least a rotational movement around a rotation axis of the rotating part. The detector unit comprising at least one detector configured to provide a Panoramic image, a computed tomography image, and a Cephalometric image, and the rotating part further comprising moving means. The computer program comprises a positioning code for positioning by means of the moving means the at least one detector relative to the rotating part for the imaging and an imaging code for providing the Panoramic, computed tomography, or Cephalometric image by means of the at least one detector.

One embodiment of the invention is a tangible nonvolatile computer readable medium comprising a computer program for controlling an X-ray imaging unit, when the computer program is run in a computer. The unit comprises a rotating part comprising a first X-ray source and an X-ray imaging detector unit configured to provide an image by means of at least a rotational movement around a rotation axis of the rotating part. The detector unit comprising at least one detector configured to provide a Panoramic image, a computed tomography image, and a Cephalometric image, and the rotating part further comprising moving means. The computer program comprises a positioning code for positioning by means of the moving, means the at least one detector relative to the rotating part for the imaging and an imaging code for providing the Panoramic, computed tomography, or Cephalometric image by means of the at least one detector.

Further embodiments of the invention are defined in dependent claims. The features recited in depending claims are mutually freely combinable unless otherwise explicitly stated.

The definitions of the below-defined verbs and terms shall be applied, unless a different definition is given in the claims or elsewhere in this description/specification.

The verb "to comprise" is used in this document as an open limitation that neither excludes nor requires the existence of unrecited features. The verbs "to include" and "to have/has" are defined as to comprise.

The terms "a", "an" and "at least one", as used herein, are defined as one or more than one and the term "plurality" is defined as two or more than two. The term "another", as used herein, is defined as at least a second or more.

The term "or" is generally employed in its sense comprising "and/or" unless the content clearly dictates otherwise.

BRIEF DESCRIPTION OF THE FIGURES

The embodiments of the invention will be described with reference to the accompanying Figures, in which.

DETAILED DESCRIPTION OF THE FIGURES

Figure 2A:
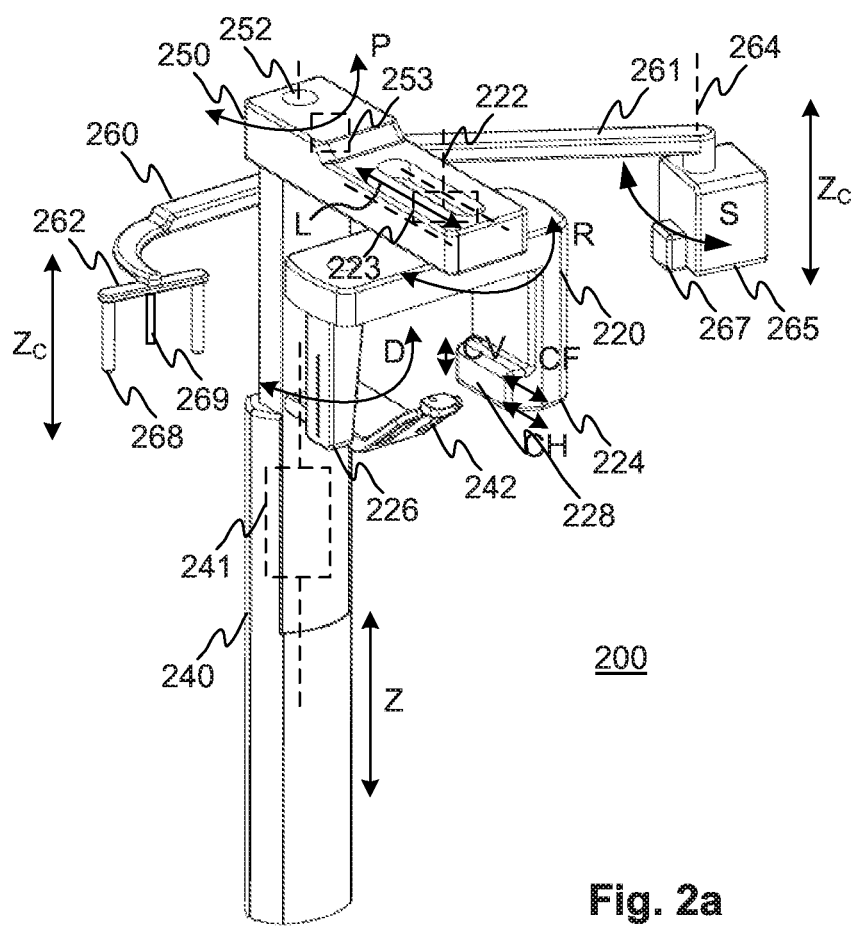
FIG. 2a represents an X-ray imaging unit for a medical imaging and its main parts and movements.

FIG. 2a represents main parts of an X-ray imaging unit 200, which can be used in medical imaging, e.g. in extraoral dental imaging.

The unit 200 includes a rotating part (gantry) 220, which includes an X-ray unit which includes a first X-ray source 224. An X-ray imaging detector unit (head) 226 is attached to the rotating part 220. A position of the detector unit 226 can be adjustable, e.g. the detector unit 266 is rotable or movable in a linear fashion. The X-ray source 224 and/or the detector unit 226 provides e.g. a Panoramic, CT, or Cephalometric image by means of at least a rotational movement R around a rotation axis 222 of the rotating part 220. The R-movement of the rotating part 220 is e.g., up to 400 degrees around the rotation axis 222.

The rotating part 220 includes a rotating motor, which is configured to rotate the rotating part 220 by means of rotation means (not shown). Alternatively, the rotating motor can be in an upper shelf 250 of the unit 200.

The rotating part 220 has e.g. a form approximating a letter C and the X-ray source 224 is on one end of the rotating part 220. The X-ray source 224 is common for two imaging modes—the Panoramic imaging and CT imaging, e.g. the CBCT imaging, where an X-ray beam is a cone-shaped beam. In additional CT imaging techniques, the X-ray beam can be a pyramidal-shaped beam, half-moon -shaped cone beam, or other shaped beam.

In addition, the X-ray source unit includes a beam limiting device 228 for the X-ray source 224 and a beam limiting motor configured to adjust the device 228. During imaging the beam limiting device 228 controls the size and shape of the X-ray beam so that it matches the needs of a selected imaging protocol, selected image size, and related detector size.

Figure 2B:
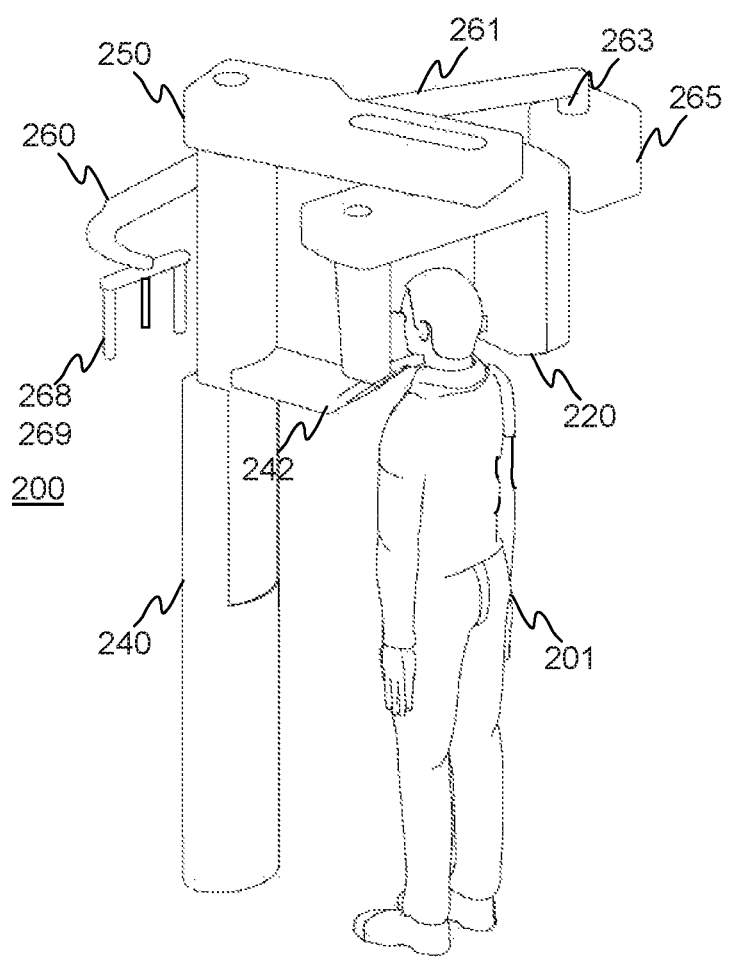
FIG. 2b represents an X-ray imaging unit and a patient in a Panoramic/CT imaging position during an imaging.
Figure 2C:
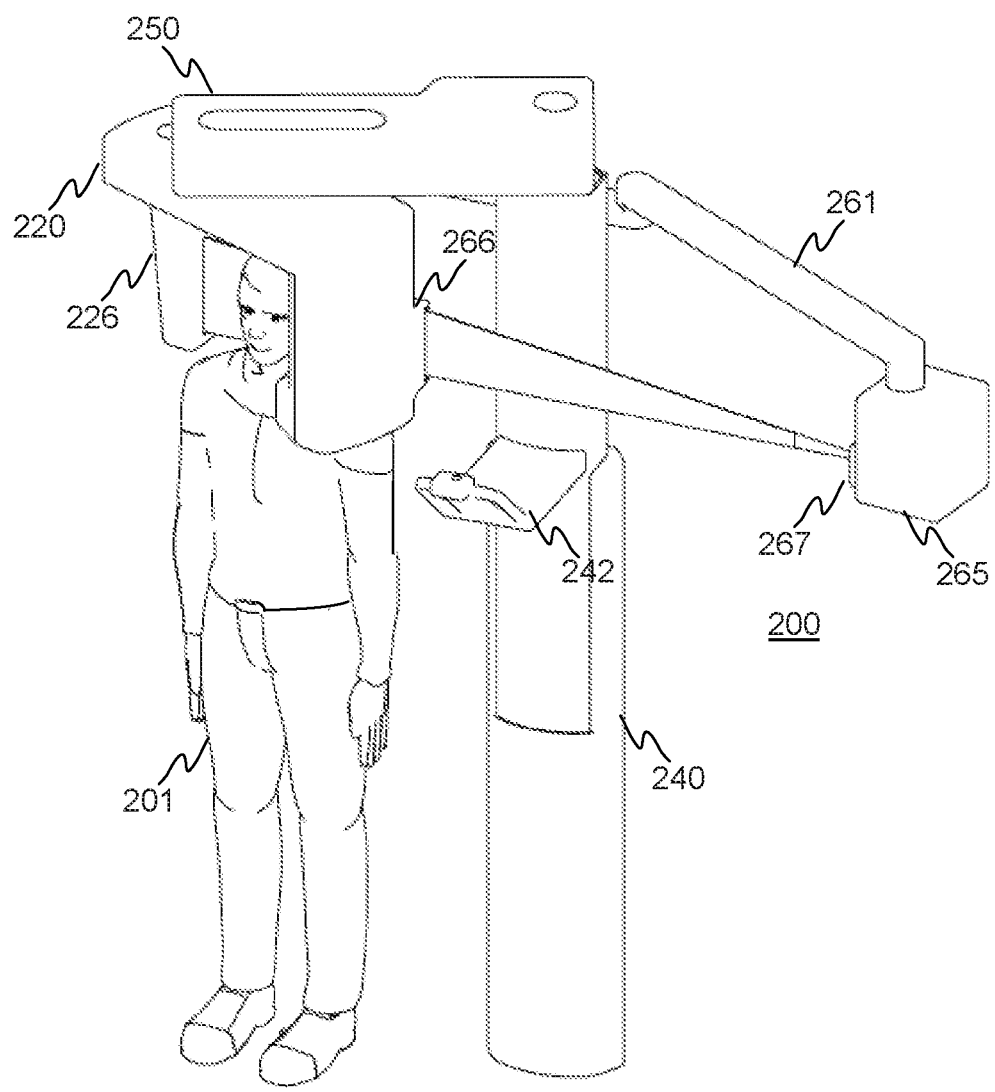
FIG. 2c represents an X-ray imaging unit and a patient in a Cephalometric imaging position during an imaging.
Figure 2D:
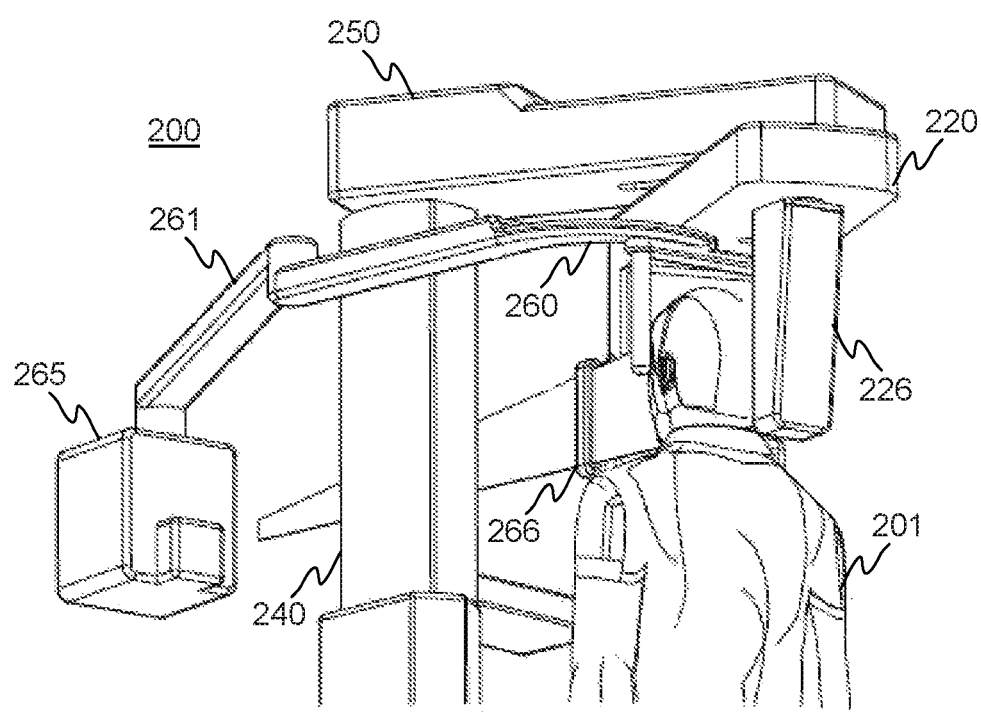
FIG. 2d represents a Cephalometric collimator used in Cephalometric imaging.
Figure 2E:
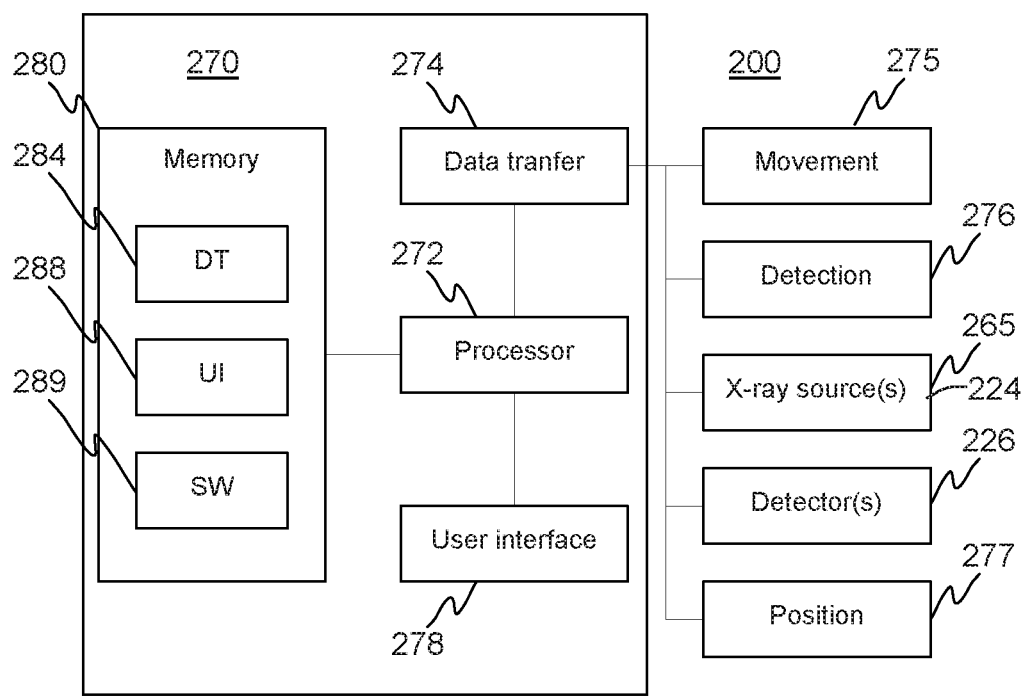
FIG. 2e represents functional elements of the X-ray imaging unit.
Figure 2F:
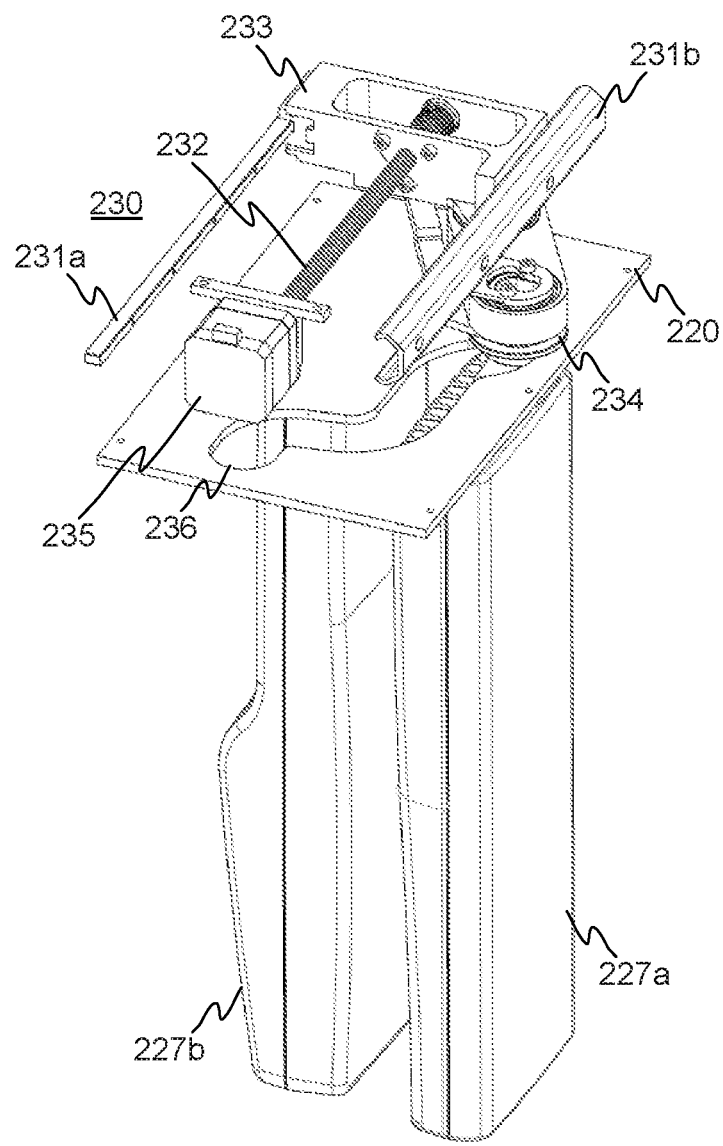
FIG. 2f represents an exemplary embodiment of a two detector X-ray imaging unit, exemplarily configured in a Panoramic imaging position.
Figure 2G:
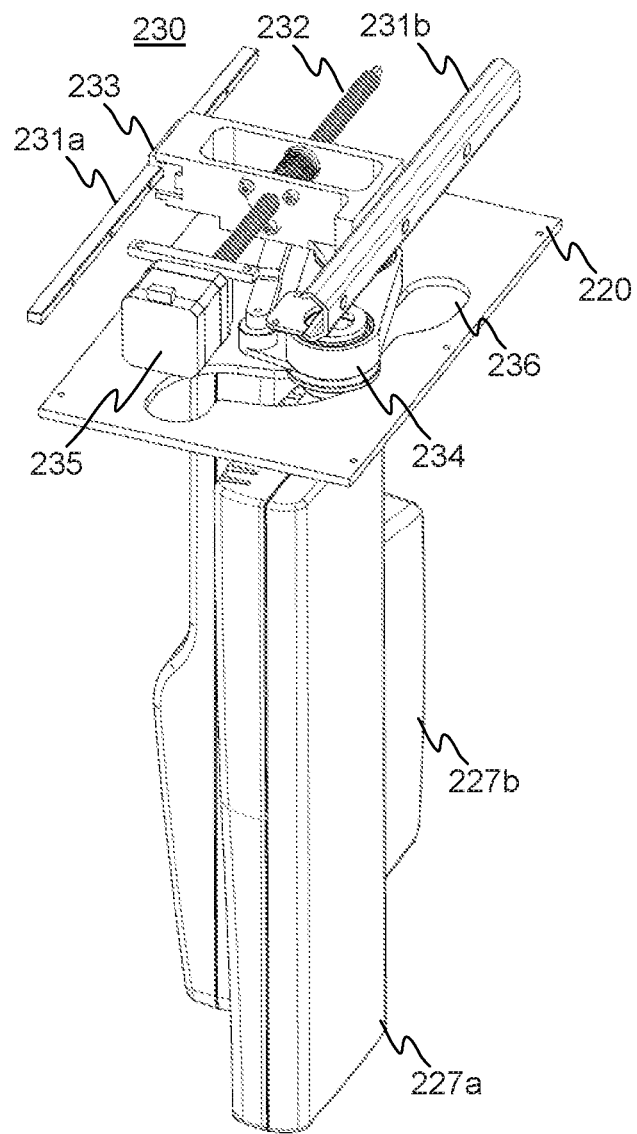
FIG. 2g represent an exemplary embodiment of a two detector X-ray imaging unit, exemplarily configured between a Panoramic imaging position and a CT imaging position.
Figure 2H:
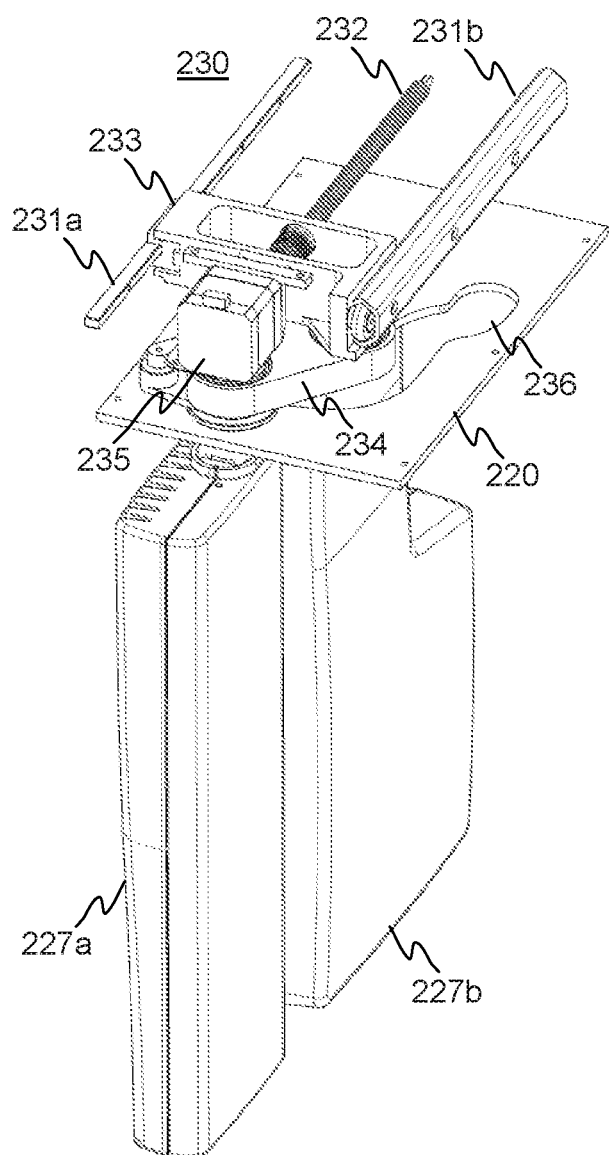
FIG. 2h represents an exemplary embodiment of two detector X-ray imaging unit, exemplarily configured to another CT imaging position.

On the other end of the rotating part 220 is the detector unit 226, which can include e.g. one or two X-ray detectors 227a, 227b (see FIGS. 2f-2h). An exemplary embodiment of a one-detector X-ray unit 226 can include one X-ray detector 227 which may include one Panoramic detector, one Cephalometric detector, which enables also the Panoramic imaging, one Panoramic/CT combination detector, one Panoramic/CT/Cephalometric combination detector, or one detector configured to be used in Panoramic/CT imaging and in one-shot Cephalometric imaging.

The one detector X-ray detector unit can be adjustable, e.g. by rotating the detector unit 226 relative to the rotating part 220 so that the one detector of the detector unit 226 can be positioned preferably perpendicularly to the used X-ray source 224 or 265 (described in further detail herein) and/or by moving one detector or detector unit 226 in a linear fashion relative to the rotating part 220 for adjusting a distance between the one detector or detector unit 226 and the X-ray source 224 in Panoramic/CT imaging.

In an exemplary embodiment of a two-detector X-ray detector unit 226, the detector unit 226 can include one Panoramic detector and one CT detector 227b, or one Cephalometric detector 227a, which enables also the Panoramic imaging, and the CI detector 2271). In a two-detector embodiment of the detector unit 226, the detectors are arranged e.g. successively in Panoramic imaging, whereupon the Panoramic or Cephalometric detector 227a is arranged as a front detector for arranging magnification ratio for the imaging mode, and the CT detector 227b as a rear detector. The swap of the detectors 227a, 227b is arranged so that the front detector 227a moves aside by means of moving means 230, e.g. a rail 231a, 231b and a rotator configured to move along the rail 231a, 231b and to rotate so that the front detector 227a slides e.g. next to a rear detector 227h, when it is necessary to use the rear detector 227a in CT imaging or the front detector 227a in Cephalometric imaging. Alternatively, the front detector 227a can be moved to another position relative to the rear detector 227b in Cephalometric imaging. The place of the front detector 227a in Cephalometric imaging may depend upon on how the front detector 227a is displaced by means of the swap movement, and the R- and L-, movements relative to the used X-ray source 265. The Cephalometric detector 227a can be positioned preferably perpendicularly to the used X-ray source 265. The front detector 227a returns similarly by sliding, when it is necessary to move the front detector 227a back to the front position.

The rotating part 220 can comprise a detector motor 235 configured to move at least one detector by means of the moving means 230, if the detector unit 226 includes separate detectors 227a, 227b for the Panoramic and CT imaging.

In addition, the unit 200 includes a column 240 for adapting a height Z of the unit 200—and the rotating part 220. The column 240 comprises height adapting means 241 which may include e.g. a height motor, a gear, and a threaded rod, and telescopic or counter weighted means configured to be driven by the height motor, for providing an up/down movement Z to adapt the height of the rotating part 220 to the height of the patient 201 for the Panoramic, Cephalometric, or CT imaging modes. The height adapting means 241 can realize the Z-movement e.g. as a movement of the height adapting means and/or as a telescopic or counter-weighted movement.

A lower shelf 242 is attached to the column 240 and the rotating part 220 is configured to be positioned over the lower shelf 242 during the Panoramic and CT imaging. The lower shelf 242 is used for positioning a patient 201 for the Panoramic and/or CT imaging and for supporting the patient 201 e.g. from a tip of the patient's 201 chin during the imaging.

Alternatively, when the unit 200 includes a seated patient's 201 positioning system (not shown), the Z-movement is realized e.g. by adapting in the Z-direction the height of at least one of the following: a chair, the lower shelf 242, and the column 240.

The lower shelf 242 can also include a head support (not shown), which supports e.g. the patient's 201 forehead and/or temple in the Panoramic/CT imaging position.

The unit 200 includes said upper shelf 250, which supports the rotating part 220. The upper shelf 250 is attached to e.g. an upper end of the column 240 with a pivoting joint (means) 252, which enables a pivot movement P of the upper shelf 250 around the column 240 and in respect to a lower shelf 242 so that the rotating part 220 is over e.g. the lower shelf 242.

The upper shelf 250 includes pivot movement means 253, which includes e.g. a pivot motor 253 configured to pivot the upper shelf 250 around the column 240 by means of the pivoting joint 252.

The upper shelf 250 includes linear movement means 223, e.g. a linear conveyor configured to support the rotation means of the rotating part 220 and to enable the rotating part 220 to rotate around the rotation axis 222, at least one rail and/or track configured to guide the linear conveyor in the upper shelf 250, and a linear motor configured to drive the linear conveyor along the at least one rail and the upper shelf 250, which enable the rotating part 220 and the rotation means to move with respect to the upper shelf 250 by means of a linear movement L. The linear movement means 223 of the upper shelf 250 can be provided so that L movement in a plane of the upper shelf 250 is a direct linear movement, e.g. it is parallel to the upper shelf 250 or it is in a certain angle with respect to the parallel direction, or the L-movement in the plane of the upper shelf 250 is a non-direct linear movement having e.g. a curved path or a devious path.

The rotation means attach the rotating part 220 to the upper shelf 250. The rotation means are able to move with at least one L-movement so that the axis 222 and, thus, the rotation center in respect to the upper shelf 250 can be adjusted along the L-movement. Thus, the axis 222 can be positioned within a plane defined by the P-movement of the upper shelf 250 and the L-movement of the rotating part 220 during the imaging.

Figure 1A:
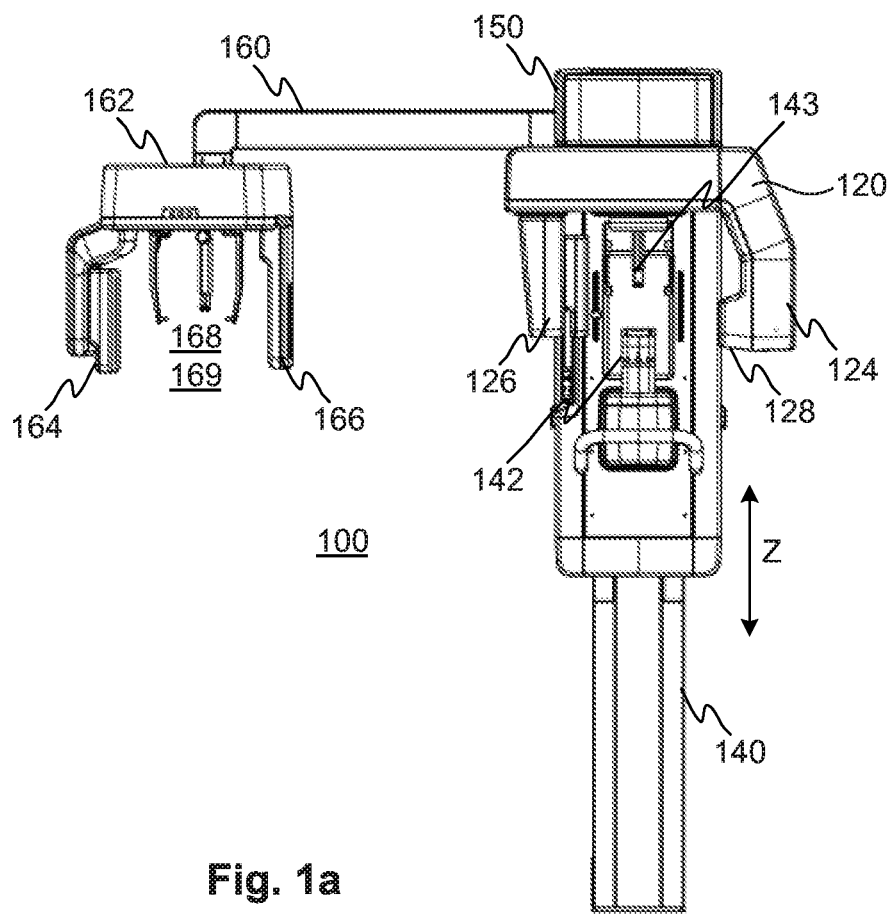
FIGS. 1a-1b represent a known digital Panoramic/Cephalometric/CT combination unit from the front and from above.
Figure 1B:
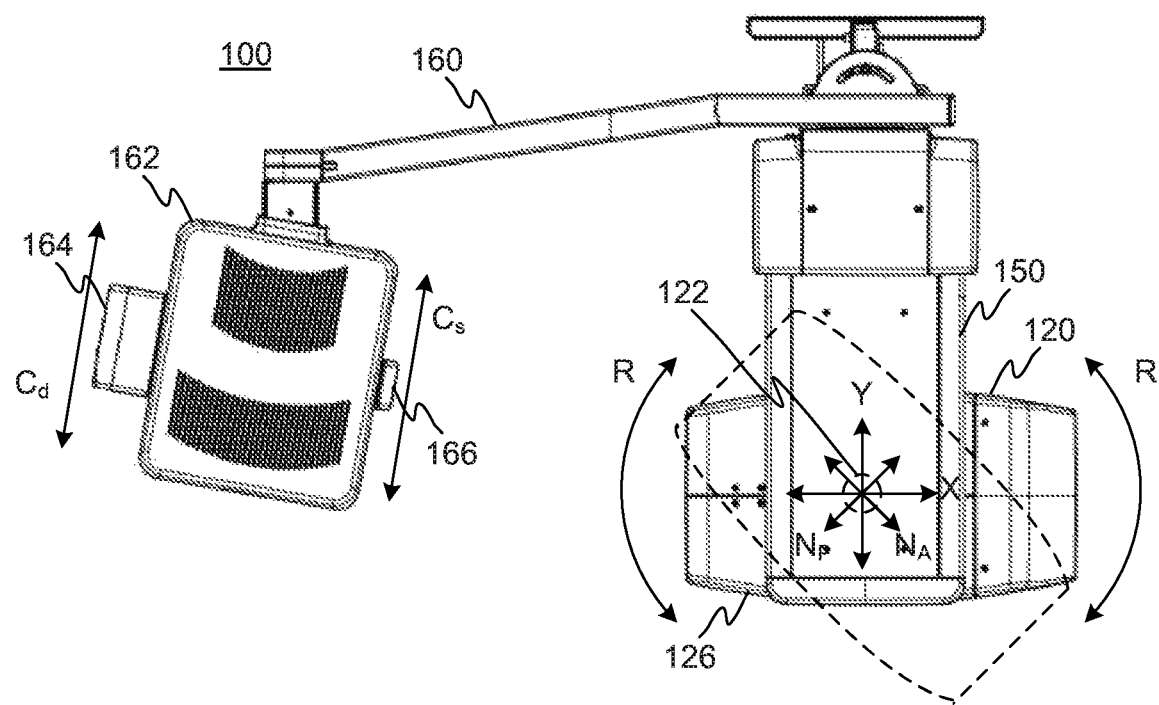

By using a rotating P-movement, rather than a linear X-movement, to adjust the lateral position of the rotating axis 220, it is possible to design much lighter and thinner upper shelf 250, thus giving the unit 200 a smaller footprint. In contrast, the conventional method of relying on a linear X-movement requires a wider upper shelf 250, and relying on an NP-movement requires a wider rotation part 220, as depicted in FIG. 1b.

The X-ray source 224 on the one end of the rotating part 220 typically weighs more than the detector unit 226 on the other end. As a result, a movement of the center of the gravity of the rotating part 220 can cause a varying load to a joint construction (not shown) of the rotating part 220, which includes the linear movement means 223, so that the rotating part 220 wobbles during the imaging and, thus, reduces the image quality.

In order to eliminate these problems, the upper shelf 250 includes a controlling arrangement (not shown) that enables the R-movement of the rotating part 220 in relation to the upper shelf 250 so that the axis 222 travels substantially with the center of the gravity of the rotating part 220, which, in turn, stays in a neutral axis of the joint construction of the rotating part 220 during the imaging. A virtual rotation axis of the rotating part 220 is achieved by synchronizing R-, L-, and P-movements during the scanning.

The controlling arrangement, by operating the rotating part 220 in the manner described above, removes any torque applied to the joint construction and increases an image quality by removing artifacts caused by wobbling.

In addition, the controlling arrangement enables to produce a lighter, cheaper, and slender structure of the rotating part 220 and its joint construction.

In addition, the unit 200 includes on one side of the column 240 a first Cephalometric arm 260 that has a certain first length. The arm 260 attaches a Cephalometric head (unit) 262 to the unit 200 at a certain first distance that corresponds with the first length from the column 240.

The Cephalometric head (support) 262, which has a significantly simpler structure than in traditional Cephalometric units, includes Cephalometric patient support means 268, 269, e.g. two ear rods 268 and a nose (nasion) support 269, for supporting the patient 201 to be imaged. The patient's 201 head is supported e.g. from an outer part of the ear canal with the ear rods 268 and from the nose using the nose support 269. The ear rods 268 and nose support 269 can be attached to the Cephalometric head 262 in a manner that enables them to rotate e.g. to two main imaging positions: lateral and PA projections. The lateral projection is basically a side view and the PA projection is from back to front view of a skull of the patient 201.

The ear rods 268 can be tiltable or rotable ear rods having a down position, where the ear rods 268 support the patient 201, and an up position, where it is possible to place the patient 201 in the Cephalometric imaging position or where the patient 201 can depart from the Cephalometric imaging position, when the tilted or rotated ear rods 268 in the up position provide a clear passage of the patient 201.

In addition, the unit 200 may include on other side of the column 240 a second Cephalometric arm 261 that has a certain second length. Attached to the second Cephalometric arm 261 is a second X-ray source 265, which is used in Cephalometric imaging. The second Cephalometric arm holds the second x-ray source at a second distance from the unit 200, corresponding to a second length from the column 240. The X-ray source 265 includes a beam limiting device 267 for the Cephalometric imaging. Optionally, the beam limiting device 267 can be attached to the X-ray source 265. The X-ray source 265 can be configured to rotate around a rotation axis 264 by means of rotation means 263 configured to perform a scanning movement S. The axis 264 of the X-ray source 265 is in line with a focal spot of the X-ray source 265 so that it passes through the focal spot. The arm 261 or the X-ray source 265 includes a rotating motor, which is configured to rotate the X-ray source 265 around the axis 264, which coincides with the focal spot of the X-ray source 265.

The arms 260, 261 can be separate arms attached to the column 240, or it is possible to use one arm 260, 261, which includes the Cephalometric head 262 in its one end and the X-ray source 265 with the beam limiting device 267 in the other end of the single arm 260, 261.

FIG. 2d illustrates how the Cephalometric, combination, or one-shot detector of the detector unit 226 attached to the rotating part 220 can be used to perform Cephalometric imaging.

In addition, FIG. 2d shows that the rotating pan 220 can include a Cephalometric (secondary) collimator 266, which is used in the Cephalometric imaging together with one detector of the detector unit 226. The Cephalometric collimator 266 is attached, e.g., to one (right) side of the rotating pan 220 (e.g. X-ray source 224), as depicted in FIG. 2c. Alternatively, the Cephalometric collimator can be attached e.g. to another (left) side of the rotating part 220 (e.g. X-ray source 224).

In addition, the rotating part 220 can include a detector motor 235 configured to rotate at least one detector of the detector unit 226 for the Cephalometric imaging, and a collimator motor configured to adjust a position (height) of the Cephalometric collimator 266 in the Z-direction and/or a position of the collimator of the X-ray source 224. Alternatively, or in addition, the beam limiting motor or the collimator motor can be configured to adjust both the device 228 and the Cephalometric collimator 266.

The rotating part 220 is driven over the Cephalometric head (support) 262, e.g. with the P-, R-, and L-movements, so that the detector unit 226 and the Cephalometric collimator 266 are positioned for the Cephalometric imaging.

The X-ray source 265 can be configured to provide, together with e.g., the detector unit 226 (e.g. the Cephalometric detector 227a attached to the detector unit 226) and the Cephalometric collimator 266 in the rotating part 220, a Cephalometric image from the positioned patient 201, when it is rotated around the axis 264 by means of the S-movement, and the detector unit 226 and the Cephalometric collimator 266 are arranged to move e.g. by means of at least one of the P-, R-, and L-movements of the rotating part 220. Alternatively, the scanning movement of the x-ray beam—e.g. a linear S-movement—can be performed by moving the beam limiting device 267 of the X-ray source 265.

If the one-shot detector is used, the detector unit 226 and the Cephalometric collimator 266 are positioned by means of at least one of the P-, R-, and L-movements, but the image can be taken without these movements and/or without the S-movement.

Thus, there is no need for a dedicated holder or the $C_s$-movement for the detector unit 164 and the $C_d$-movement of the Cephalometric collimator 166, when the scanning movement is executed with e.g. the P-, R-, L-, and S-movements.

The arms 260, 261 can be arranged so that a height of the Cephalometric head 262 with the ear rods 268 and nose support 269 is fixed relative to the X-ray source 265.

However, the fixed height may cause problems, because an anatomy of patients 201 varies—e.g., the vertical distance where ear openings are located compared to patient's 201 shoulders differs significantly from one patient 201 to another. Thus, either the patient 201 is located too low in the resultant Cephalometric image, showing only upper vertebras, or the patient 201 is located so high in the images that the shoulder of the patient 201 touches the detector unit 226, which is a problem especially with a scanning. Furthermore, the preferred Cephalometric imaging geometry requires that the focal spot and the tips of the ear rods 268 are at the same (horizontal) axis.

In order to eliminate these problems, variable length ear rods 268 can be used while keeping the arms 260, 261 fixed height relative to each other.

Alternatively or in addition, in order to eliminate these problems, the unit 200 can comprise Cephalometric height adjusting means (not shown) that are configured to independently adjust the height—in respect to the column 240—of the arms 260, 261 that support the Cephalometric head 262 at the one end and the X-ray source 265 on the other end.

When the operator has adjusted the height of the arms 260, 261 by means of an up/down $Z_c$-movement, the focal spot follows the tips of the ear rods 268 automatically and, thus, the geometry (ear rod tip to focal spot line) remains intact. Yet, the detector unit 226 and the Cephalometric collimator 266 on each side of the patient 201 take their height from the column 240 and, thus, are on a different height in respect to the ear rods 268 and the patient 201 than before the adjustment.

The Cephalometric height adjusting means provides a way to adapt an exposed area to a given anatomy of the patient 201 by enabling an operator (user) to adjust the height of the patient 201 without compromising the geometry.

Since the first and second X-ray sources 224, 265 can be arranged at different heights with respect to the column 240 in the Z direction by means of the height adapting means 241 and/or the Cephalometric height adjusting means, it is possible to position the patient 201 without any additional adjustment of the Cephalometric head 262 in the Z direction as it is needed when using the X-ray source 224 of the rotating part 220 for the Cephalometric imaging.

The movements of unit 200 are simple, because the traditional X-movement, as well as the $C_d$- and $C_s$-movements of the detector unit 226 and the secondary collimator 266 in the Cephalometric head 262, are replaced by using the P-movement instead. The movements are carried out using the L-movement and the P-movement of the upper shelf 250.

In addition, by using the P-movement, the structure of unit 200 is made simpler and cheaper, because the Cephalometric imaging can optionally be implemented by using only one "non-detachable" detector unit 226. This reduces the risk of breaking the detector unit 226 because there is no need to remove it from a holder of the rotating part 220 to detach it from a holder of the Cephalometric head 262 when changing the imaging mode from the Panoramic/CT mode to the Cephalometric mode. The detector for the Panoramic imaging in the detector unit 226 can be rotated from the Panoramic imaging position to the Cephalometric imaging position so that it is possible to use the same detector in both Panoramic and Cephalometric imaging.

In addition, the structure of unit 200 provides a simple workflow when e.g. the change from the Panoramic/CT mode to the Cephalometric mode—the movement of the rotating part 220 from the Panoramic/CT imaging position to the Cephalometric position without changing the detector unit 226 from one holder to other holder—is automated, thus decreasing both the amount of manual work required and the time needed for the work flow.

It is also possible that the unit 200 includes the upper shelf 250 that pivots around the column 240 and the rotating pan 220 that is configured to be positioned by means of the above-described L- and P-movements for providing the Panoramic and/or CT imaging, but has a more conventional Cephalometric head 262 comprising the Cephalometric detector, the secondary collimator, and the patient positioning support parts.

Cephalometric imaging is provided by means of the X-ray source 224 of the rotating part 220, and the secondary collimator and the Cephalometric detector of the Cephalometric head 262. The X-ray source 224 is arranged to scan the patient's 201 head with the R- and L-movements. The X-ray beam is collimated by the secondary collimator and captured by the Cephalometric detector, which are synchronized with the X-ray beam.

It is also possible that the unit 200 is provided so that it comprises only one X-ray source, which has several positions for providing the Panoramic, CT, and Cephalometric imagings. The one X-ray source is positioned relative to the rotating part 220 during the imagings.

FIG. 2b represents a positioning of the patient 201 during the Panoramic/CT imaging.

The patient 201 is supported by the lower shelf 242 and possibly to the head support of the unit 200 in a Panoramic/CT imaging position, where the rotating part 220 is over the lower shelf 242.

If the upper shelf 250 as well as the rotating part 220 are in a different position than the Panoramic/CT imaging position—in a Cephalometric imaging position or in an intermediate position between e.g. the Panoramic/CT and Cephalometric imaging positions—the upper shelf 250 is moved from that position to the Panoramic/CT imaging position by the P-movement and, then, the rotating part 220 is further adjusted by the R- and L-movements so that the rotating part 220 is ready for the Panoramic/CT imaging.

In addition, the rotating part 220 can have a patient positioning position, where the X-ray source 224 or the detector unit 226 are out of the way and do not interfere with the positioning of the patient 201 to the Panoramic/CT and/or Cephalometric imaging positions when the rotating part 220 is over the lower shelf 242 or the Cephalometric head 262. The patient positioning position can be accomplished by the R-movement so that the rotating part 220 is rotated to such position, where it is possible to place the patient 201 to the Panoramic/CT and/or Cephalometric imaging positions or to remove the patient 201 by moving the patient's 201 head between the X-ray source 224 and the detector unit 226. Alternatively, it is possible to realize the patient positioning position by means of the P-movement, whereupon the whole rotating part 220 is moved away from the Panoramic/CT and/or Cephalometric imaging positions, when the patient 201 is positioned.

The positioned X-ray source 224 and the detector unit 226 are configured to provide a Panoramic image when the rotation axis 222—a rotation center of the rotating part 220—is positioned by at least one of the P- and L-movements.

Depending on the sensor technology used, the image can be clocked out using, a TDI mode or a full frame read-out mode of the detector. In the TDI mode, the image is read out one column at a time, whereas in the full frame mode, the image is read out whole image frame at a tune. The Panoramic (sharp) layer is defined by the velocities of the movements and, in the case of TDI, the readout rate of the Panoramic detector. When using a full frame detector, the final shape of the layer is calculated on the computer after the scan. Rotation angle is typically about 270 degrees, but this is not intended to be limiting.

During the CT imaging, the patient 201 is also supported by the lower shelf 242 and possibly by the head support of the unit 200 in the Panoramic/CT imaging position. The X-ray source 224 and the detector unit 226 are configured to provide a CT image when the detector unit 226 is attached to the rotating unit and the rotation center of the rotating part 220 is positioned so that it can coincide with the ROI.

The positioned X-ray source 224 and the detector unit 226 are configured to provide a CT image, e.g. CBCT image, when the detector unit 226 is attached to the rotating unit 220, and the rotation axis 222 is positioned by at least one of the R-, L-, and P-movements during the CT imaging.

When the unit 200 is used with a symmetric imaging geometry, the CT imaging can be carried out by using only the R-movement and reading out the CT detector in a full frame mode. Alternatively, or in addition, CT imaging can be carried out by using the P-, R-, and L-movements, using the controlling arrangement in the upper shelf 250, for positioning the virtual rotation axis of the rotating part 220 so that it coincides the ROI. Thus, projection X-ray images of the ROI are produced in a way that the center of the ROI and the R-movement coincide. In an embodiment, the effective rotation angle (aperture) ranges e.g. from approximately 180 to 360 degrees depending on the unit 200.

When the unit 200 is used in an offset imaging, the CT imaging can be carried out by scanning the image by using the R-, L-, and P-movement. By driving these R-, L-, and P-movements in synchronism, the effective center of the rotation can be deflected to the side of the beam and, thus creating an offset geometry.

The offset scanning can be provided by a first "solid" offset geometry and a full 360 degree rotation of the CT detector.

Alternatively, the offset scanning can be provided by a second offset geometry, where the patient 201 is imaged by scanning an essentially maximal first imaging offset with approximately 180 degree rotation of the detector in a first imaging direction. Then, the detector is displaced to the other side of the rotation center to obtain art essentially maximal second imaging offset by approximately 180 degree rotation of the detector in a second imaging direction, which is opposite to the first direction. Alternatively, the detector is rotated to the starting position, displaced to the other side of the rotation center, and, then, scanning the essentially maximal second imaging offset by approximately 180 degree rotation in the first direction.

Alternatively, the offset scanning can be provided by a third offset geometry, where the patient 201 is imaged by a first imaging offset, where the edge of the X-ray beam area touches the rotation center, and by 360 degree rotation of the detector, Next, the detector and the X-ray source 224 are displaced parallel in such a way that the X-ray beam area moves away from the rotation center so it hits or slightly overlaps the previously imaged area. Then, the detector is rotated 360 degrees for completing a second imaging offset.

The unit 200 provides same versatility in the CT imaging geometry by means of the R-, and P-movements instead of the R-, X-, and N-movements required in imaging and patient positioning by some conventional systems.

FIG. 2c represents a positioning of the patient 201 during the Cephalometric imaging.

In the Cephalometric imaging position, where the rotating part 220 is over the patient support means 268, 269 located at the Cephalometric head 262, the patient 201 is supported to the patient support means 268, 269.

If the upper shelf 250 as well as the rotating part 220 are in a different position than the Cephalometric imaging position—e.g. in a Panoramic/CT imaging position or in an intermediate position between the Panoramic/CT and Cephalometric imaging positions—the upper shelf 250 is moved from that position to the Cephalometric imaging position by the P-movement, and then the rotating part 220 is further adjusted by the R- and L-movements so that the rotating part 220 is ready for the Cephalometric imaging.

The positioned X-ray source 265 is configured to scan the supported patient 201 by means of the beam limiting device 267 attached to the X-ray source 265 and by means of the S-movement. The detector unit 226—and the rotating part 220—is configured to move synchronously with the X-ray source 265 by the R-, L-, and P-movements during the Cephalometric imaging.

The X-ray beam from the X-ray source 265 is arranged to scan the patient's 201 head by rotating the X-ray source 265 and the beam limiting device 267 with the S-movement around the axis 264. Alternatively, the S-movement can be performed by moving (e.g., linearly) the beam limiting device 267. It is also possible that the S-movement is provided as a vertical scanning movement instead of the horizontal S-movement, if the detector of the detector unit 226 used in Cephalometric imaging is positioned horizontally. Alternatively, Cephalometric imaging can be performed without the S-movement if a sufficiently large detector (so-called oneshot detector) is used for the one-shot Cephalometric image.

The beam is then further collimated by the Cephalometric collimator 266 and finally captured by the synchronously moved Cephalometric or combination detector in the detector unit 226.

The unit 200 simplifies the movements during the Cephalometric imaging, because no additional movement means are needed for the Cephalometric collimator 266 and the detector of the detector unit 226.

FIG. 2e represents the functional elements of the unit 200.

The unit 200 includes a control unit (control panel) 270 that is configured to control the unit 200, and its above-described movements and imaging processes. The control unit 270 are attached e.g. to the column 240.

The control unit 270 includes at least one processor (portion) 272 for performing user and/or software initiated instructions and for processing data, and at least one memory (portion) 280 for storing and maintaining data, e.g. instructions, software, and data files.

In addition, the control unit 270 includes a data transfer portion 274 for sending control commands to e.g. the pivot, linear, height, rotating, detector, beam limiting, and collimator motors, drivers, or other means (motors, devices) 275 configured to provide the movements of the parts of the unit 200, and/or receiving data from measuring devices or other detection devices 276 configured to detect the function of parts of the unit 200.

In addition, the data transfer portion 274 is also configured to send control. commands to the at least one of followings: at least one of X-ray source 224 and/or X-ray source 265, the detector unit 226, and positioning means 277, e.g., at least one laser, camera, or other indication means, configured to facilitate a positioning of the patient 201 in the Panoramic imaging position and/or CT imaging position by indicating a correct positioning of the patient 201. The data transfer portion 274 is also configured to receive information from at least one of the following: the at least one X-ray source 224, 265, the detector unit 226, and the positioning means 277.

In addition, the control unit 270 includes a user interface portion 278 which may include at least one of the following: at least one function key, a touchscreen, and a wired or wireless remote controller, for inputting control commands, and for receiving information and/or instructions.

The at least one memory 280 stores at least a data transfer application 284 for execution by the processor 272 controlling the data transfer portion 274, a user interface application 288 for execution by the processor 272 for controlling the user interface portion, and a computer program (code) 289 for controlling the function of the unit 200, e.g., at least the movement devices 275, detection devices 276, the at least one X-ray source 224, 265, the detector unit 226, and positioning means 277. In addition, execution of the computer program 289 can control e.g. imaging, parameters, imaging sizes, and imaging modes.

The at least one memory 280 and the computer program 289 are configured to, with the at least one processor 272, cause the unit 200 at least to provide actions described in context of FIGS. 2a-2d, e.g. to control positions of the detector unit 226 and the Cephalometric collimator 266 by at least one or two of the R-, L-, and P-movements.

The computer program 289 can be a computer program product that comprises a tangible, non-volatile (non-statutory) computer-readable medium bearing a computer program code 289 embodied therein for use with a computer (control unit 270).

FIG. 2f represents one detector unit 226 that includes at least one detector 227a, 227b, which can provide a Panoramic, CT, and Cephalometric image.

The rotating part 220 includes moving means 230, which move the at least one 20 detector 227a, 227b relative to the rotating part 220 for positioning the at least one detector 227a, 227b for the imaging, and the detector motor 235 configured to drive the moving means 230.

The detector 227a can be e.g. a Panoramic detector, which is configured to provide the Panoramic image, or a Cephalometric detector, which is configured to provide a Cephalometric image and a Panoramic image. The CT detector 227b is configured to provide a CT image.

The moving means 230 can comprise e.g. at least one of rails 231a, 231b, threaded rod 232, a conveyor unit 233, a guide unit 234 that is connected to the conveyor unit 233 and attaches the detector 227a to the rotating unit 220, and a guide groove 236.

The detector motor 235 moves the detector 227a by means of the threaded rod 232, which moves the conveyor unit 233 along the rails 231a, 231b so that the guide unit 234 guides the detector 227a sideways along the guide groove 236 that can be e.g. a direct, curved, or devious groove.

FIG. 2f represents one example of a Panoramic imaging position, wherein the X-ray source 224 and the Panoramic or Cephalometric detector 227a, which is attached to the rotating unit 220, can provide the Panoramic image.

The detector 227a and the CT detector 227b are arranged successively in the Panoramic imaging position so that the detector 227a is between the X-ray source 224, 265 and the CT detector 227b—the detector 227a is in front of the CT detector 227b relative to the used X-ray source 224, 265.

FIG. 2g represents how the detector motor 235 drives (swaps) the detector 227a along the curved groove 236 between the Panoramic imaging position and a CT imaging position.

FIG. 2h represents one example of the CT imaging position, wherein the detector 227a and the CT detector 227h are arranged substantially next to each other side by side.

The CT imaging position can also be a Cephalometric imaging position, wherein the X-ray source 265 can provide together with the Cephalometric detector 227a, which is attached to the rotating unit 220, the Cephalometric image.

It is possible that the detector 227a is in another position relative to the CT detector 227b in Cephalometric imaging, e.g. in the position according to FIG. 2g or in a position, wherein the detector 227a is displaced so that it is substantially behind the CT detector 227b.

In addition, it is possible that the Cephalometric imaging can be provided when the detectors 227a, 227b are arranged successively, whereupon the Panoramic imaging position is also the Cephalometric imaging position.

Figure 2I:
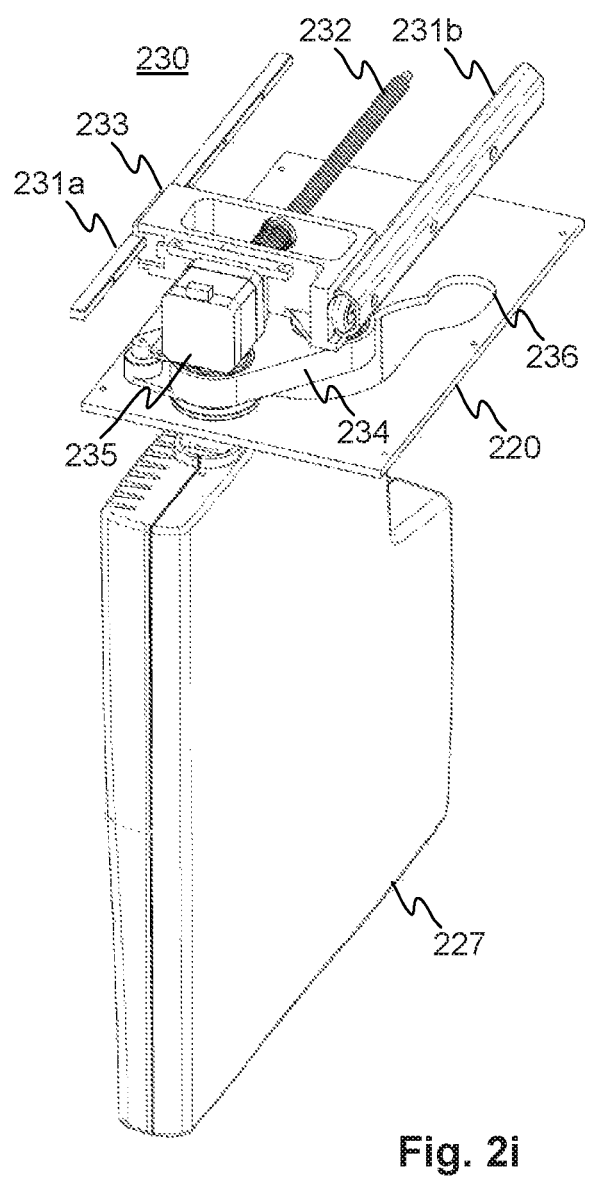
FIG. 2i represents an exemplary embodiment of a one detector X-ray imaging unit.

FIG. 2i represents a one-detector unit 226 that comprises one combination detector 227, which can provide a Panoramic, CT, and Cephalometric image.

The first X-ray source 224 and the combination detector 227, which is attached to the rotating part 220, are used for providing the Panoramic image and the CT image. The second X-ray source 265 and the combination detector 227, which is attached to the rotating part 220, are used for providing the Cephalometric image.

The combination detector 227 can be driven similarly as the detector 227a in the two detectors unit 226 represented in FIGS. 2f-2h by e.g. similar moving means 230, but not necessary by all its movements.

The Panoramic image is taken when the combination detector 227 has been driven to the Panoramic imaging position similarly as represented in FIG. 2f, whereupon the combination detector 227 is in a front position.

The CT and Cephalometric images are taken when the combination detector 227 has been driven to the CT/Cephalometric imaging position similarly as represented in FIG. 2h, whereupon the combination detector 227 is in a back position.

In addition, the combination detector 227 can be positioned by means of the moving means 230 and by means of at least one of the R-, L-, and P-movements. Alternatively, the combination detector 227 can be positioned by means of at least one of the L-, and P-movements.

So, the combination detector 227 can be moved between at least of two of the Panoramic, CT, and Cephalometric imaging positions by means of the moving means 230 and/or by means of at least one of the R- and P-movements.

The invention has been now explained above with reference to the aforesaid embodiments and the several advantages of the invention have been demonstrated. It is clear that the invention is not only restricted to these embodiments, but comprises all possible embodiments within the scope of the invention thought and the following claims.

The invention claimed is:

1. An X-ray imaging unit for medical imaging, the X-ray imaging unit comprising:
    a column;
    an upper shelf coupled to the column through a joint configured to enable a pivot movement (P) of the upper shelf with respect to the column;
    a rotating part rotatably coupled to the upper shelf and having a rotation axis with respect to the upper shelf, the rotating part movable to at least a first imaging position and a second imaging position, the rotating part comprising a first X-ray source and an X-ray imaging detector unit, the first X-ray source and the X-ray imaging detector unit configured to provide an image by means of at least a rotational movement (R) of the rotating part;
    a second x-ray source; and
    a first patient positioning means for panoramic and computed tomographic imaging, the first patient positioning means defining a first patient position of a patient to be imaged and a second patient positioning means for cephalometric imaging, the second patient positioning means defining a second patient position of the patient to be imaged;
    wherein the upper shelf is configured to enable the rotation axis to move with respect to the upper shelf by means of a linear movement (L), and the rotating part is moved by at least the pivot movement between the first imaging position wherein the rotating part is configured to provide the image between the first X-ray source and the X-ray imaging detector and the second imaging position wherein the rotating part is configured to provide the image between the second X-ray source and the X-ray imaging detector; and
    wherein the rotating part is positioned by at least the pivot movement of the upper shelf over the first patient positioning means at the first imaging position to provide at least one of a panoramic image and a computed tomography image, and the rotating part is positioned by at least the pivot movement of the upper shelf over the second patient positioning means at the second imaging position to provide at least one cephalometric image.

2. The X-ray imaging unit of claim 1, wherein the rotating part is configured to be positioned by at least one of the rotational, linear and pivot movements during a panoramic imaging.

3. The X-ray imaging unit of claim 1, wherein the rotating part is configured to be positioned by at least one of the rotational, linear, and pivot movements during a computed tomography imaging.

4. The X-ray imaging unit of claim 1 wherein the patient positioning means comprises a lower shelf adapted to position a patient to be imaged at a first patient position for the panoramic and/or computed tomography imaging, and the rotating part is configured to be positioned over the lower shelf at the first imaging position by at least the pivot movement of the upper shelf.

5. The X-ray imaging unit of claim 1, further comprising a control unit which operates to move the rotating part by controlling the linear movement and the pivot movement of the rotating part during the imaging.

6. An X-ray imaging unit for medical imaging, the X-ray imaging unit comprising:
   a column;
   an upper shelf coupled to the column through a joint configured to enable a pivot movement (P) of the upper shelf with respect to the column;
   a rotating part rotatably coupled to the upper shelf and having a rotation axis with respect to the upper shelf, the rotating part comprising a first X-ray source and an X-ray imaging detector unit, the first X-ray source and the X-ray imaging detector unit configured to provide an image by means of at least a rotational movement (R) of the rotating part; and
   a second x-ray source, wherein the upper shelf is configured to enable the rotation axis to move with respect to the upper shelf by means of a linear movement (L), and the rotating part is moved by at least the pivot movement between a first imaging position wherein the rotating part is configured to provide the image between the first X-ray source and the X-ray imaging detector and a second imaging position wherein the rotating part is configured to provide the image between the second X-ray source and the X-ray imaging detector, and the second X-ray source is configured to provide, together with the detector unit, a cephalometric image when the rotating part is in the second imaging position by at least the pivot movement of the upper shelf; and
   a first arm configured to attach a cephalometric head to the column, comprising a cephalometric patient support configured to support the patient to be imaged at a second patient position, wherein the second imaging position of the rotating part is in alignment with the second patient position; and
   a second arm configured to attach the second X-ray source to the column.

7. The X-ray imaging unit of claim 6, wherein the second X-ray source comprises a beam limiting device, and the second X-ray source is configured to perform a scanning movement (S) by at least one of rotating around a rotation axis of the second X-ray source and moving the beam limiting device.

8. The X-ray imaging unit of claim 7, wherein the rotation axis of the second X-ray source passes through a focal spot of the second X-ray source.

9. The X-ray imaging unit of claim 7, wherein the second X-ray source is configured to scan the patient by means of the beam limiting device attached to the second X-ray source and the scanning movement, and the detector unit is configured to move synchronously with the second X-ray source by the rotational, linear, and pivot movements during cephalometric imaging.

10. The X-ray imaging unit of claim 6, wherein the rotating part comprises a cephalometric collimator configured for cephalometric imaging and the rotating part is configured to be positioned over the cephalometric head at the second imaging position by the pivot movement.

11. The X-ray imaging unit of claim 1 configured to be adapted by means of a height movement (Z).

12. The X-ray imaging unit of claim 11, wherein the column comprises the height adapting means configured to adapt a height (Z) of the rotating part.

13. The X-ray imaging unit of claim 11 further comprising height adapting means configured to perform the height movement (Z) by a telescopic or counter weighted movement.

14. A method for controlling an X-ray imaging unit comprising a column, an upper shelf coupled to the column through a pivoting joint for enabling a pivot movement (P) of the upper shelf with respect to the column, a rotating part rotatably coupled to the upper shelf and having a rotation axis with respect to the upper shelf, the rotating part comprising a first X-ray source and an X-ray imaging detector unit, and a second X-ray source, the method comprising:
   positioning the rotating part with at least the pivot movement of the upper shelf with respect to the column to position the rotating part in either a first imaging position wherein the rotating part is configured to provide imaging between the first X-ray source and the X-ray imaging detector and a second imaging position wherein the rotating part is configured to provide imaging between the second X-ray source and the X-ray imaging detector; and
   acquiring a plurality of images by means of at least a rotational movement (R) of the rotating part at either of the first imaging position or the second imaging position,
   wherein when a patient is positioned at a first patient position in alignment with the first imaging position, operating the first X-ray source and the detector together to acquire the plurality of images that include panoramic images or tomography images; and
   wherein when the patient is positioned at a second patient position in alignment with the second imaging position, operating the second X-ray source and the detector to acquire the plurality of images that include cephalometric images.

* * * * *